Figure 1:
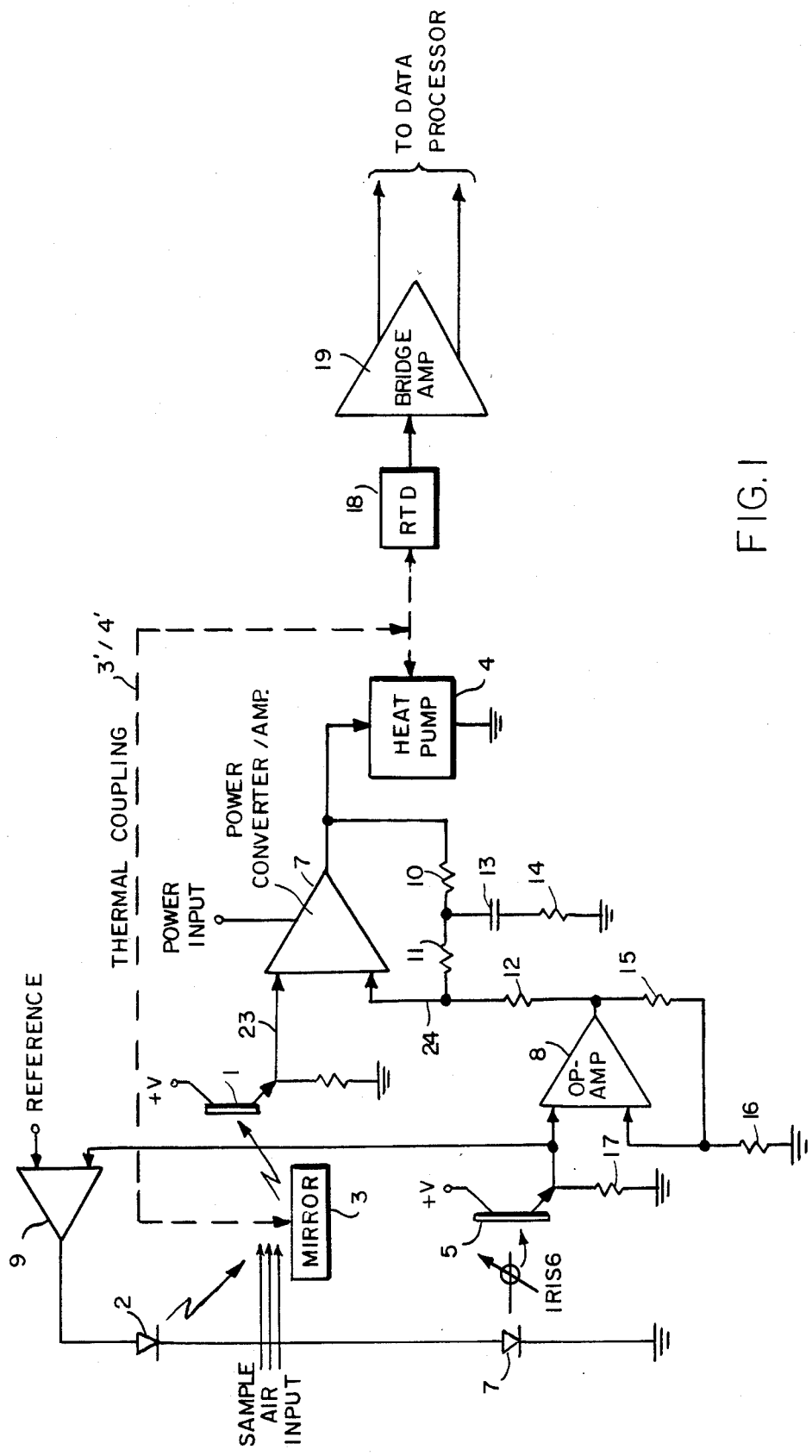

United States Patent [19]

Harding, Jr.

[11] Patent Number: 4,554,793
[45] Date of Patent: Nov. 26, 1985

[54] CONTROLLED POWER CONVERTER FOR THERMOELECTRIC HEAT PUMP DRIVE

[75] Inventor: John C. Harding, Jr., Framingham, Mass.

[73] Assignee: General Eastern Instruments Corporation, Watertown, Mass.

[21] Appl. No.: 502,475

[22] Filed: Jun. 9, 1983

[51] Int. Cl.⁴ ............................................. G10N 31/00
[52] U.S. Cl. .......................................... 62/126; 73/29; 374/20
[58] Field of Search ...................... 323/288, 282; 62/3, 62/129, 126, 176.1; 236/46 F; 73/29; 374/20

[56] References Cited

U.S. PATENT DOCUMENTS

| | | | |
|---|---|---|---|
| 3,383,584 | 5/1968 | Atherton | 323/288 X |
| 3,733,540 | 5/1973 | Hawkins | 323/288 X |
| 3,959,714 | 5/1976 | Mihelich | 323/288 |
| 4,016,461 | 4/1977 | Roland | 323/282 X |
| 4,030,015 | 6/1977 | Herko et al. | 323/288 X |
| 4,216,669 | 8/1980 | Harding, Jr. | 73/29 X |

Primary Examiner—Harry Tanner
Attorney, Agent, or Firm—Robert O'Connell

[57] ABSTRACT

A controlled power conversion system for providing power to a thermoelectric heat pump for controlling the temperature of a device, such as a chilled mirror used in a chilled mirror humidity sensor. The system uses means, responsive to a DC input power source and to a control signal representing changes in the temperature of the device, for providing periodic pulses of the DC input power having a duty cycle which is controllable in accordance with the control signal. The input power is time-averaged and an energy storage means, responsive to the periodic pulses of DC input power, is utilized to provide a controllable time averaged DC power output to the heat pump.

15 Claims, 3 Drawing Figures

CONTROLLED POWER CONVERTER FOR THERMOELECTRIC HEAT PUMP DRIVE

This invention relates generally to controlled electrical power conversion techniques used for driving thermoelectric heat pumps and, more particularly, to the use thereof in systems for cooling an optically reflective surface to its temperature of condensation for providing a dew point measurement of a sampled atmosphere.

BACKGROUND OF THE INVENTION

Thermoelectric (Peltier) heat pump devices are essentially an array of thermocouples arranged in parallel to pump heat from one region to another. When used to cool a mirror surface, for example, heat is pumped from the reflective surface of the mirror to the surface on the opposite side. Although the array of elements are arranged in a series configuration electrically, the electrical resistance across the input terminals of the heat pump is very low, usually a fraction of an ohm. A typical heat pump input power requirement, for example, is 1.0 volt at 2.5 amperes. The heat pumping rate and, therefore, the temperature depression is controlled by the magnitude of the electrical power input. Heat pumps are normally driven by conventional linear power amplifiers which must be designed, with suitable dynamic range, for such purposes. Such linear power amplifiers, however, usually dissipate more power internally than is provided to the heat pump for pumping heat so that the overall system is extremely inefficient. In addition, the current drain on the input power source is very often intolerable in many applications. The input power requirement which has in the past been necessary for using a heat pump in cooling a mirror surface to its condensation point to measure humidity, for example, has in fact made the use of such linear power amplifier/heat pump combinations impractical for such a purpose, particularly in situations where large numbers of such humidity sensors are required, as in large industrial energy management systems.

It is desirable to provide a method and system of temperature control for humidity sensors in which power that is available on an input power line is converted efficiently on a demand basis for driving the thermoelectric heat pump therein in accordance with an input control signal. Such a system should provide suitable power conversion in which the internal power dissipation and, therefore, the input power requirement is reduced to a realizable minimum. The use of such a controlled power conversion technique should permit the use of a heat pump in humidity measuring instruments in which the overall level of performance represents a substantial improvement, at a reasonable and reduced cost, over that used by prior art humidity measuring systems.

BRIEF SUMMARY OF THE INVENTION

In accordance with the invention a power conversion/amplifier circuit provides suitable control signal amplification and output power for driving a thermoelectric heat pump in a manner such that efficient conversion of available input power is achieved. The circuit of the invention effectively comprises a power switch circuit which provides variable DC power to the thermoelectric heat pump by periodically completing the circuit path between the input power line and the heat pump. The ratio of "ON" time to "OFF" time of the power switch is modulated by an input control signal so as to vary the heat pumping rate. Energy storage circuits at both the power input and power output lines provide time averaging of the pulsed input power and pulsed power output signals, respectively. By using such controlled operation, available input power is converted at a relatively high efficiency as required by the thermoelectric heat pump to maintain the desired temperature control.

The power converter/heat pump combination can be used to great advantage, for example, in a humidity measuring system in which an optically reflective surface is cooled to its condensation temperature so that the dew point of a sampled atmosphere can be measured and, hence, the water vapor concentration, or humidity, can be determined. The control signal depends on the reflectance state of the surface which state can be suitably sensed so that the heat pump power is controlled by the cooling "demand" required to bring the surface to, and to maintain the surface at, the condensation temperature.

DESCRIPTION OF THE INVENTION

Figure 2:
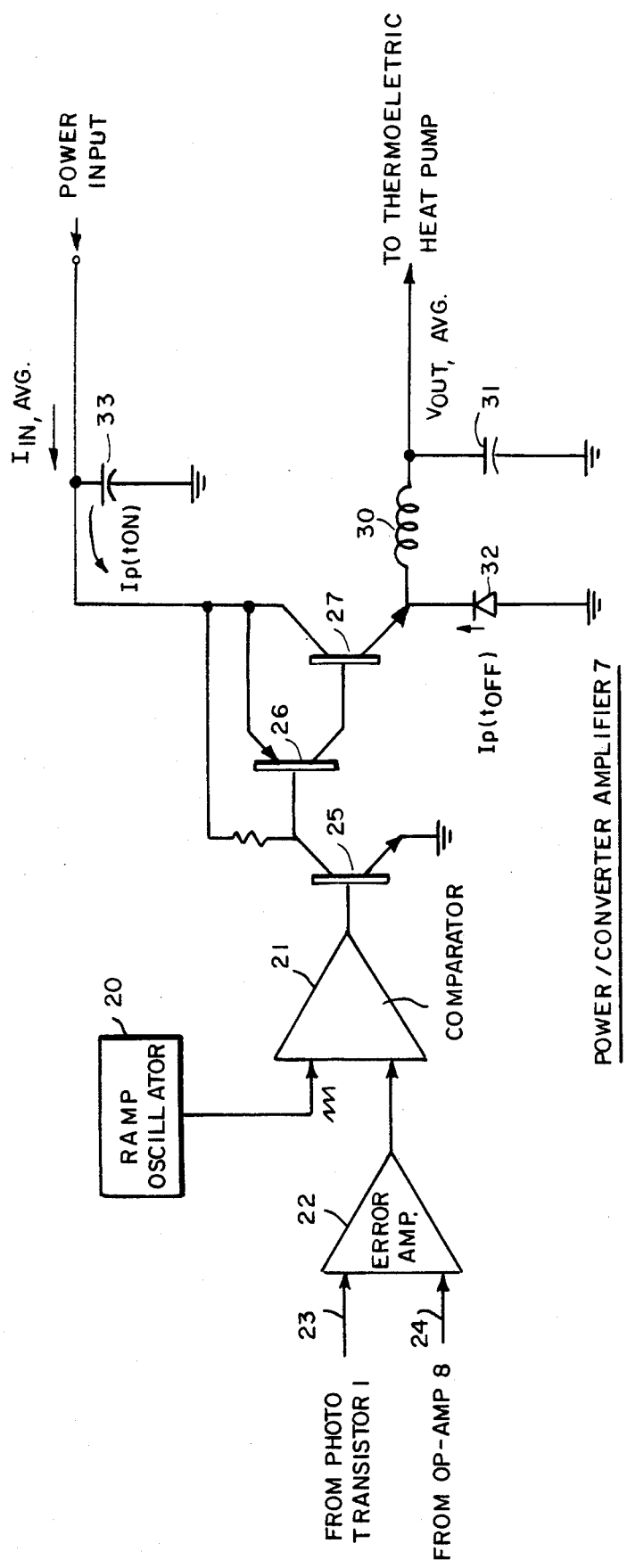
Figure 3:
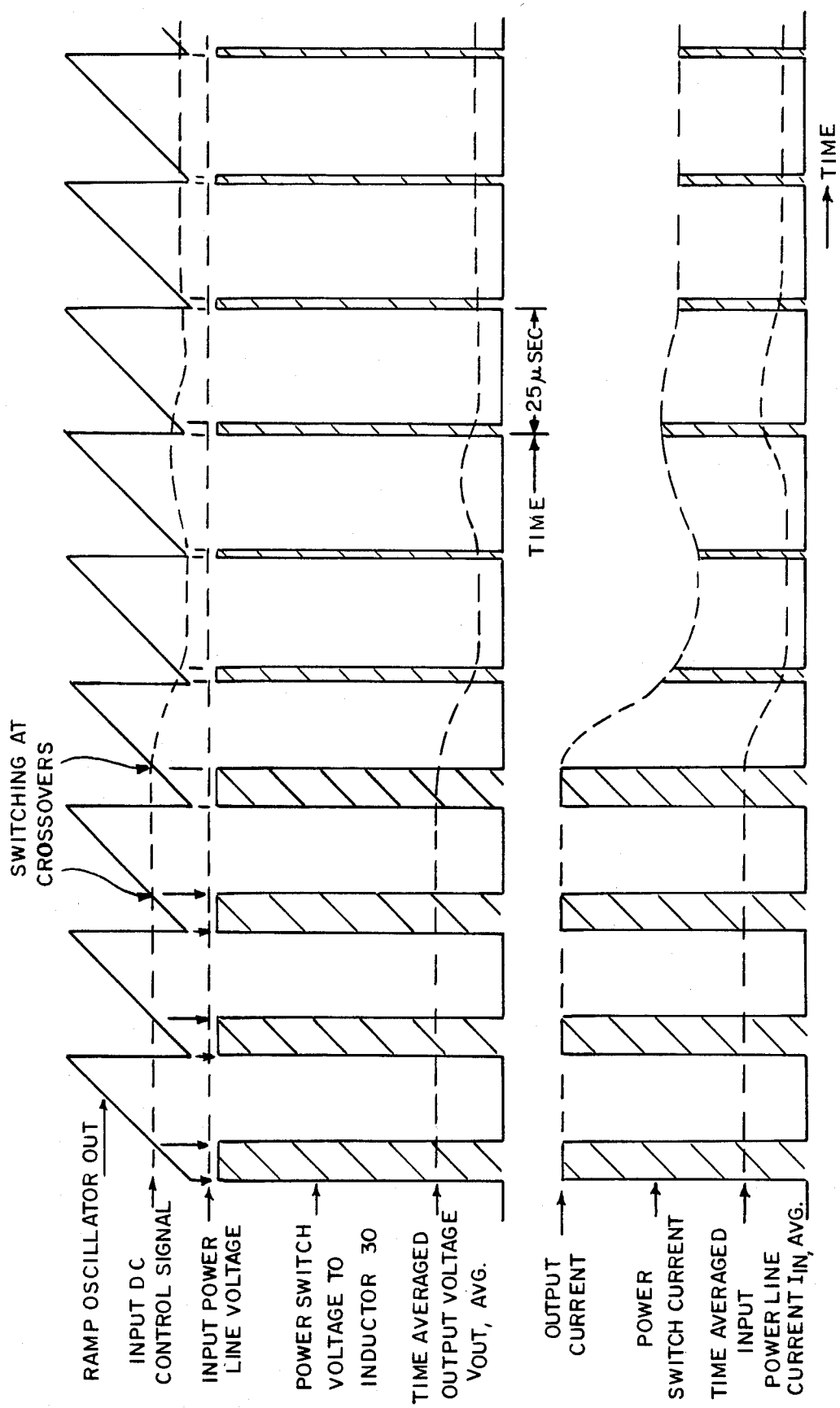

The invention can be described in more detail with the help of the accompanying drawings wherein FIG. 1 shows a partial block diagram, partial schematic circuit diagram of a condensation hygrometer system using the invention;

FIG. 2 shows a more detailed partial block diagram, partial schematic circuit diagram of the switching power converter/amplifier portion of the system of FIG. 1; and FIG. 3 shows representations of waveforms of various voltages and currents illustrating the operation of the circuit diagram of FIG. 2.

Since the power conversion technique of the invention can be effectively used to drive a thermoelectric heat pump in a humidity measurement system which requires the cooling of a reflective surface to its condensation temperature, the invention is specifically described herein with reference to such a system. Such description is not intended to limit the use of the power conversion technique of the invention only to such application, inasmuch as other applications therefor will occur to those in the art in the light of the description presented here. For the purpose of describing the invention in the above mentioned context it is helpful to review briefly the operation of a humidity measuring system of the type described.

Measurement of the temperature of condensation of a sampled atmosphere has been long recognized as a superior method of humidity determination because of the fundamental physical relationship between dew point and water vapor concentration. This relationship exists because the saturation vapor pressure of any pure substance is specific to the substance and its temperature only. A condensation hygrometer controls or maintains the surface temperature of a hydrophobic material, which is exposed to the sampled atmosphere, at an equilibrium temperature, i.e., the temperature at which no further evaporation or condensation occurs once an operating dew layer is established. The equilibrium condition can only occur at the temperature where the saturation vapor pressure equals the partial pressure of the condensable gaseous constituent, which in such a system is water. The partial pressure of the constituent gas is in turn proportional to its concentration in the gas mixture according to Dalton's Law which states that the partial pressure is that pressure which a constituent gas would exert if it were to occupy the total volume of the mixture. Humidity determination by the condensation method, therefore, reduces the problem to one of surface temperature measurement.

Fortunately there are in existence the materials and means by which temperature can be measured accurately and repeatably. platinum, which is a noble and inert metal, for example, exhibits a very specific relationship between bulk electrical resistivity and temperature when pure and annealed, or strain free. Calibrated industrial grade platinum resistance temperature transducers are available which can easily provide 0.1° C. accuracy over a 100° range for many years in the absence of any recalibration. It is, therefore, both possible and practical to implement a condensation hygrometer system that provides a total, long-term dew point measurement uncertainty of 0.2° C., which corresponds to 1% Relative Humidity if one assumes equivalent accuracy in the air temperature measurement. Herein lies an outstanding advantage inherent to such technique since virtually all other methods of humidity determination involve a secondary, or indirect, method. In one such latter method, the bulk capacitance or resistance of certain organic materials or metal oxides which readily absorb water vapor, for example, are measured for humidity determination. These devices are nonlinear, are sensitive to temperature, exhibit hysterisis, require individual calibration, and typically do not hold their original calibration characteristics in that they are subject to aging and contamination effects.

Some limitations associated with the condensation method, however, have created difficulties and have deterred widespread applications therefor in such areas as heating, ventilation, air conditioning and various industrial process control systems, for example. Until recently, application of the condensation method has been confined primarily to laboratory and certain industrial instrumentation. The most significant limitations, which have discouraged use in high volume applications, include the lack of total automation, the constraint by which humidity is displayed in terms of dew point, certain contamination effects and related maintenance requirements, as well as operating and relatively high power consumption requirements. The advent of low cost, large scale integrated circuits, particularly microprocessor chips, along with other recent improvements such as described in U.S. Pat. No. 4,216,669 issued on Aug. 12, 1980 to John C. Harding, Jr. and in co-pending U.S. application, Ser. No. 474,739, filed on Mar. 10, 1983, by John C. Harding, Jr. The improvements disclosed therein have served to overcome most of these limitations. The problem of excessive power consumption, however, has not been effectively addressed by the prior art and automatic condensation hygrometers which employ thermoelectric heat pumps for cooling the surface where condensation occurs still suffer from such problem.

The system particularly described herein overcomes the power consumption problem in accordance with the invention. The operation of a typical condensation hygrometer is well described in the aforesaid Harding patent and patent application and need not be described in detail here, except as needed for an understanding of the invention set forth in the context thereof. A block diagram of such a system (sometimes referred to as a "chilled mirror" hygrometer) is shown in FIG. 1. As can be seen therein a photo transistor 1 is positioned so as to observe specular reflectance from a light source 2, which may be, for example, a light emitting diode (LED). The light from LED 2 is directed toward a mirror 3 which is in thermal contact with a thermoelectric heat pump 4 as shown by the dashed line 3'/4' which diagrammatically represents a thermal coupling between mirror 3 and heat pump 4. The reflecive surface of mirror 3 is cooled by the operation of the heat pump to its temperature of condensation.

A reference photo transistor 5 is used to provide a temperature tracking differential input current signal which is offset with respect to the signal current from photo transistor 1 by a fixed amount when the mirror is in a dry condition. Such temperature tracking reference is necessary because the gain, or transfer function, of photo transistors changes considerably with ambient temperature. Thus, photo transistor 5 receives light from an LED 7 via an adjustable iris 6, the output of photo transistor 5 being supplied to a conventional operational amplifier (op-amp) 8 having a fixed gain. When the mirror 3 is in a completely dry condition the amount of light from LED 7 which impinges on photo transistor 5 is adjusted by adjusting the opening of iris 6 to produce a photo current from photo transistor 5, via op-amp 8, which is offset with reference to the photo current from photo transistor 1. In a particular embodiment this off-set, or bias, photo current is adjusted so that the photo current at op-amp 8 is 35% below that from photo transistor 1, so that the heat pump is driven in a manner so as to produce a maximum pumping of heat, i.e., a maximum rate of cooling, of the surface of mirror 3.

Further, the system uses a temperature compensation reference loop wherein the output of photo transistor 5 is supplied to one input of a feedback differential op-amp 9 for comparison with a suitably selected reference voltage at the other input of op-amp 9 to change the current through LED's 2 and 7 if the temperature of the photo transistor 5 varies. The reference level is selected to provide a known current from photo transistor 5 at a known operating temperature. Accordingly, if the operating temperature of photo transistor 5 (as well as the temperature of photo transistor 1 which is in the same temperature environment) changes, the current through the LED's is automatically adjusted to produce the same photo transistor output current. Accordingly, the relationships between the photo current outputs of the two photo transistors remain the same independently of operating temperature changes. A similar temperature compensation scheme is discussed in the above-mentioned Harding patent application.

The difference (initially the original offset) between photo currents of transistors 1 and 5, when amplified, causes the thermoelectric heat pump to cool the mirror surface to the temperature at which condensation begins to form thereon. The formation of condensation on the mirror surface in turn causes a reduction in the signal current of photo transistor 1, thereby reducing the above photo current differential and, hence, reducing the power drive to the heat pump 4. Condensation continues to form on the surface until the offset in differential photo current is essentially nulled, at which point a controlled equilibrium condition exists. The density of the operating layer of condensate is, therefore, fixed by the pre-set photo current offset, or initial difference, which is set as discussed above. Once an operating dew layer is established at equilibirum, the mirror surface is maintained precisely at that temperature at which no further condensation or evaporation occurs. Such temperature is by definition the dew point.

Operational amplifier 8 provides true electrical symmetry for the differential input configuration, i.e. the gain factors from each photo current input to the output of power converter/amplifier 7 are equal but of opposite sign. Power converter/amplifier 7, in addition to providing control signal gain, performs a true conversion of available input power to output power for the thermoelectric heat pump drive. The network of resistors 10, 11 and 12 establishes the DC forward gain, while resistor 13 and capacitor 14 provide necessary frequency compensation for control loop stability.

The controlled surface temperature of the mirror which corresponds to the dew point temperature is suitably measured by the use of a precision platinum resistance temperature detector (RTD) 18 which is part of a suitable bridge/amplifier circuit 19, the output current being suitably calibrated to represent the dew point and being supplied to a user as desired. Thus, the overall system of FIG. 1 may represent one of many sensors used at various points at which environmental characteristics are measured, the outputs thereof being supplied to a data processor system where their values are processed for use in an overall control system, e.g. a heating, ventilating and air-conditioning (HVAC) system. Such data processor system does not form a part of the invention and need not be further described here. Such a system is described, for example, in the above-mentioned Harding application.

The controlled power conversion/amplification process performed by power converter/amplifier 7 can be described with reference to FIGS. 2 and 3. As seen in FIG. 2, an oscillator 20 provides in a preferred embodiment a triangular ramp waveform output signal at 40 kHz, for example to one differential input of a voltage comparator 21. An error amplifier 22 provides a DC gain for the error, or control signal which is the difference between the mirror photo current at line 23 and the reference photo current at line 24 from photo transistors 1 and 5, respectively. The output of error amplifier 13 is supplied to the other differential input of comparator 21. As seen with reference to FIG. 3, the comparator output changes state each time the value of the triangular ramp output at one input thereof crosses the value of the input DC control signal at the other input thereof, so that, as the control signal magnitude varies, the pulse width of the resulting output voltage changes proportionally.

The pulse width modulated switching signal at the comparator output is level translated by transistor 25 to drive the power switch circuitry comprises transistors 26 and 27. The power switch completes the circuit path between the input power line 28 and the output energy storage circuit comprising inductor 30 and capacitor 31. The input power may be obtained from a suitable power supply source, e.g. one providing a nominal voltage in a preferred embodiment of 24 volts DC. Such supply being commonly employed in large scale HVAC energy management and power control systems can be any conventional un-regulated power supply and its dc voltage can vary over relatively wide limits (as much as 12-30 volts DC) without deteriment to the circuit operation.

Typically, the power switch is ON (i.e., the switch circuit is completed) for a small fraction of the total ON/OFF cycle time, as can be seen in FIG. 3. Inductor 30 and capacitor 31 accomplish time averaging of the pulsed power output so as to provide a substantially continuous DC power signal to drive thermoelectric heat pump 4. The averaged DC power is proportional to the power switch duty cycle. A Schottky diode 32 completes the current path when the power switch is in the open, or OFF, state since the nature of any inductor is such that it impedes instantaneous changes in current magnitude. It is this property or characteristic which provides for the continuous time averaged output of pulsed or switched power. Capacitor 31 reduces the output voltage ripple associated with the triangular current ripple in the inductor. Energy storage capacitor 33 in the input power line circuit delivers the peak current to the power switch when in the ON state and recharges during the substantially longer OFF period of a cycle, thereby averaging the current delivered by the input power source and eliminating the need for peak current delivery by the input power source.

As can be seen in FIG. 3, as the condensate forms on mirror 3 the input DC control signal from photo transistor 1 is reduced. Such reduction causes a reduction in the time averaged output voltage $V_{out,avg.}$, i.e. the heat pumping rate of the thermoelectric heat pump is reduced ultimately reaching an equilibrium condition at which the mirror temperature is maintained at the dew point temperature, as required. The input power line current, which is relatively small to begin with (i.e. approximately 160 mA.), also is reduced accordingly. Thus, a relatively low voltage, relatively high current (e.g., 1.0 volt, 2.5 amp.) power signal is supplied to the heat pump to provide it with its required power input level, such power signal being efficiently converted from a relatively high voltage, relatively low current (e.g., 24 volt, 160 mA.) input power signal, substantially little or no power being dissipated as wasted power.

Thus, the circuit of FIG. 2 provides the required power amplification function for driving a thermoelectric heat pump in a manner that also achieves true energy conversion. This method substantially reduces the input power requirements for such heat pump drive and results in substantially decreased internal power dissipation. The low input power requirement and high efficiency of the circuit makes its use for driving a heat pump in a chilled mirror humidity measurement system extremely effective in comparison with prior art heat pump drives, particular in larger commercial energy management systems, e.g. HVAC and industrial process control systems.

Energy management HVAC systems typically employ 24 volt DC power distribution for controls and may have a requirement for many such humidity sensors. A conventional chilled mirror humidity sensor when driving the thermoelectric heat pump to the limit of its temperature depression capability would draw the heat pump drive current from the input power line via a linear power amplifier. A typical heat pump for this application may require, for example, 2.5 amperes at 1.0 volt for maximum temperature depression. Such a current requirement has normally prevented the employment of chilled mirror systems. Employment of the above-described circuit of the invention in such application, however, considerably reduces the 24 volt supply current requirement to as low as approximately 160 mA. and substantially increases the efficiency of the heat pump drive and control process.

What is claimed is:
1. A controlled power conversion system for providing power to a thermoelectric heat pump for controlling the temperature of a device, said power conversion system comprising means for supplying DC input power;

means responsive to the temperature of said device for providing a control signal representative of changes in the temperature thereof;

pulse width modulation/switching means responsive to said DC input power and to said control signal for providing periodic pulses of said DC input power having a duty cycle controllable in accordance with said control signal;

means for providing time averaging of said input power; and energy storage means responsive to said periodic pulses of DC input power for providing a controllable time averaged DC power output to said heat pump.

2. A system in accordance with claim 1 wherein said pulse width modulation/switching means includes means for supplying a periodic reference signal having a selected waveform;

amplifier means responsive to said control signal for amplifying said control signal;

means responsive to said periodic reference signal and to said amplified control signal for providing a periodic switching signal having a duty cycle which is proportional to said control signal; and power switching means responsive to said DC input power and to said periodic switching signal for providing said periodic pulses of said DC input power.

3. A system in accordance with claim 2 wherein said periodic switching-signal providing means comprises a voltage comparator means for comparing said periodic reference signal and said amplified control signal to produce pulses of said periodic switching signal when said amplified control signal is greater than said periodic reference signal, the duty cycle of said pulses being thereby proportional to said amplified control signal.

4. A system in accordance with claim 1, 2 or 3 wherein said periodic reference signal supplying means is an oscillator means for producing a periodic reference signal having a triangular waveform.

5. A system in accordance with 1, 2 or 3 wherein said control signal providing means comprises means for providing a first signal having a variable value representative of changes in the temperature of said component; and means for providing a second signal having a selected reference value less than the value of said first signal, the value of said control signal being the difference in the values of said first signal and said second signal.

6. A system in accordance with claim 5 wherein the value of said second signal is selected to provide a predetermined difference value when said device is in an initial uncontrolled state.

7. A system in accordance with claim 6 wherein said device is a mirror having an optically reflective surface which is to be maintained at its condensation temperature, the difference value between said first and second signals being selected so that said second signal has a value which is 35% below the value of said first signal when said optically reflective surface is in a substantially dry state at a temperature above said condensation temperature.

8. A system in accordance with claim 7 wherein said first signal providing means comprises a first light source for directing light toward said surface for reflection therefrom;

a first photo transistor means responsive to the light reflected from said surface to produce said first signal the value thereof changing as condensation forms on said surface when said heat pump thermoelectrically cools said mirror.

9. A system in accordance with claim 8 wherein said second signal providing means comprises a second light source for directing light toward a second photo transistor means to produce said second signal.

10. A system in accordance with claim 9 and further including an adjustable iris means positioned between said second light source and said second photo transistor means for controllably adjusting the light directed from said second light source to said second photo transistor means to provide a substantially constant second signal having a value selected to produce said predetermined difference value when the surface of said mirror is in said substantially dry state.

11. A system in accordance with claim 10 wherein said device and said first and second signal providing means are positioned in substantially the same ambient temperature environment and wherein said system further includes means responsive to said second signal providing means for maintaining the relationship between the first and second signals the same independently of ambient temperature changes.

12. A system in accordance with claim 11 wherein said first and second light sources are light emitting diodes and said maintaining means changes the currents through said first and second light emitting diodes so as to maintain said relationship between first and second signals independently of ambient temperature changes.

13. A system in accordance with claim 1, 2 or 3 wherein said energy storage means includes an inductance means and capacitance means forming a circuit responsive to said periodic pulses of DC input power for providing said time averaged DC power output.

14. A system in accordance with claims 2 or 3 wherein said power switching means includes transistor switching means responsive to said periodic switching signal and to said DC input power for providing said periodic pulses of said DC input power.

15. A system in accordance with claim 14 and further including Schottky diode means connected to said transistor switching means to complete a current path from said inductive means to a power return line when said switching means is in an OFF state.

* * * * *